US007239730B2

(12) United States Patent
Londt et al.

(10) Patent No.: US 7,239,730 B2
(45) Date of Patent: Jul. 3, 2007

(54) METHOD AND APPARATUS FOR VOLUME SCORING CALCIFICATION CONCENTRATIONS OF A CT SCAN

(75) Inventors: John H. Londt, Fort Wayne, IN (US); Kishore Acharya, Brookefield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 905 days.

(21) Appl. No.: 10/248,562

(22) Filed: Jan. 29, 2003

(65) Prior Publication Data

US 2004/0147838 A1 Jul. 29, 2004

(51) Int. Cl.
*G06K 9/00* (2006.01)
*A61B 6/00* (2006.01)
*A61B 5/05* (2006.01)

(52) U.S. Cl. .......................... 382/128; 378/4; 128/922; 600/425

(58) Field of Classification Search ...................... None
See application file for complete search history.

(56) References Cited

U.S. PATENT DOCUMENTS

| 4,856,528 | A | * | 8/1989 | Yang et al. ................. 382/131 |
| 5,430,783 | A | | 7/1995 | Hu et al. ...................... 378/15 |
| 5,963,614 | A | | 10/1999 | Hu et al. ...................... 378/15 |
| 6,108,575 | A | | 8/2000 | Besson ........................ 600/425 |
| 6,292,526 | B1 | | 9/2001 | Patch ............................ 378/4 |
| 6,332,013 | B1 | | 12/2001 | Hsieh ......................... 378/15 |
| 6,690,371 | B1 | * | 2/2004 | Okerlund et al. ........... 345/424 |
| 6,990,222 | B2 | * | 1/2006 | Arnold ....................... 382/131 |
| 6,996,262 | B2 | * | 2/2006 | Li ................................ 382/131 |
| 2003/0072409 | A1 | * | 4/2003 | Kaufhold et al. ............. 378/53 |
| 2004/0252870 | A1 | * | 12/2004 | Reeves et al. .............. 382/128 |

OTHER PUBLICATIONS

"Electron-Bean CT: Use of a Calibration Phantom to Reduce Variability in Calcium Quantitation", McCollough, Cynthia H., et al., Radiology 1995, vol. 196, No. 1, Jul. 1995, pp. 159-165.*
"Accurate Coronary Calcium Phosphate Mass Measurements From Electron Bean Computerd Tomograms," Detrano, Robert atal., American Journal of Cardiac Imaging, vol. 9, No. 3, Jul. 1995, pp. 167-173.*

* cited by examiner

Primary Examiner—Wenpeng Chen
(74) Attorney, Agent, or Firm—Cantor Colburn LLP (57) ABSTRACT

A method for volume scoring a concentration of calcification within a region of interest includes receiving a value for a first calcium lesion volume based on the concentration of calcification within the region of interest, determining an intensity value of the concentration of calcification within the region of interest, calculating the slope of a regression line based on the determined intensity value, and calculating a second calcium lesion volume based on the first calcium lesion volume and the calculated slope of the regression line.

28 Claims, 5 Drawing Sheets

METHOD AND APPARATUS FOR VOLUME SCORING CALCIFICATION CONCENTRATIONS OF A CT SCAN

TECHNICAL FIELD

This invention relates generally to CT scanning systems, and more particularly to a method and apparatus for volume scoring a concentration of calcification within a region of interest of a helical or axial CT scan.

BACKGROUND

Computed tomography (CT) has become the method of choice for many routine clinical studies, which includes the study of calcified plaque regions and the CT reconstruction of a projection image from projection data of a calcified plaque volume. In at least one known scanning system using a CT, an x-ray source and a detector array rotate with a gantry within the imaging plane and around the object to be imaged, such as a patient, while the patient is moved through the gantry in a direction perpendicular to the imaging plane, resulting in a constantly changing angle at which the x-ray beam intersects the scanned object. The x-ray fan beam passing through the object is attenuated before it impinges upon the array of radiation detectors. In response, the radiation detectors each produce a signal having a magnitude dependent on the intensity of the attenuated beam. The attenuation measurements from all the detectors over the duration of the scan are acquired to produce a scan profile, or set of projection data. The set of projection data resulting from the fan beam can be analyzed to reconstruct images of the scanned object.

One method of reconstructing an image of a calcified plaque volume from a set of projection data is to apply a volume scoring algorithm to calculate the calcium lesion's volume. The process applied to the projection data includes the conversion of the attenuation measurements from the scan into integers called "CT numbers" or "Hounsfield Units" (HU), which are used to control the brightness of a corresponding pixel (a 2D picture element with an intensity value) on a cathode ray tube display.

A currently used volume scoring algorithm begins by defining a calcified voxel (a 3D picture element with an intensity value) by identifying those voxels within a region of interest, such as a patient's body, that have attenuation values greater than a specified intensity and connectivity criteria. The voxel volume is then obtained by multiplying the pixel area by the thickness of each scan slice. For scans with overlapped slices, the slice thickness is adjusted by the slice spacing. The calcium lesion's volume (calcified plaque volume) is then calculated by adding the volumes of the calcified voxel volumes. The volume score is then expressed in $cm^2$ (cc) for each slice. By using voxel intensity and connectivity criteria, a volume score for the calcified plaque relating to a region of interest can be calculated. However, if the concentration of calcification within the lesion is not uniform, an error in the volume measurement will result.

SUMMARY

In one embodiment, a method for volume scoring a concentration of calcification within a region of interest includes receiving a value for a first calcium lesion volume based on the concentration of calcification within the region of interest, determining an intensity value of the concentration of calcification within the region of interest, calculating the slope of a regression line based on the determined intensity value, and calculating a second calcium lesion volume based on the first calcium lesion volume and the calculated slope of the regression line.

In another embodiment, a method for volume scoring a concentration of calcification within a region of interest includes receiving a value for a first calcium lesion volume based on the concentration of calcification within the region of interest, determining an intensity value of the concentration of calcification within the region of interest, calculating the slope of a regression line based on the determined intensity value and according to a non-linear function (y), and calculating a second calcium lesion volume based on the first calcium lesion volume and the calculated slope of the regression line.

In a further embodiment, a method for volume scoring a concentration of calcification within a region of interest includes receiving a value for a first calcium lesion volume based on the concentration of calcification within the region of interest, determining an intensity value of the concentration of calcification within the region of interest, calculating the slope of a regression line based on the determined intensity value and according to the following equation, $y=-1.13243+1.44E-02*x-2.65E-05*x^2+1.59E-08*x^3$, wherein x represents the mean intensity value of the concentration of calcification within the region of interest in Hounsfield Units and y represents the slope of the regression line, and calculating a second calcium lesion volume based on the first calcium lesion volume and the calculated slope of the regression line.

In yet another embodiment, a system for volume scoring a concentration of calcification within a region of interest includes a computer programmed to receive a value for a first calcium lesion volume based on the concentration of calcification within the region of interest, determine an intensity value of the concentration of calcification within the region of interest, calculate the slope of a regression line based on the measured intensity value, and calculate a second calcium lesion volume based on the first calcium lesion volume and the calculated slope of the regression line.

In yet a further embodiment, a system for volume scoring a concentration of calcification within a region of interest is disclosed. The system includes a computer programmed to receive a value for a first calcium lesion volume based on the concentration of calcification within the region of interest, determine an intensity value of the concentration of calcification within the region of interest, calculate the slope of a regression line based on the measured intensity value and according to a non-linear function (y), and calculate a second calcium lesion volume based on the first calcium lesion volume and the calculated slope of the regression line.

BRIEF DESCRIPTION OF THE DRAWINGS

Referring now to the figures, which are exemplary embodiments, and wherein like elements are numbered alike.

DETAILED DESCRIPTION

A detailed description of an embodiment of the present invention is presented herein by way of exemplification and not limitation with reference to the accompanying Figures.

Figure 1:
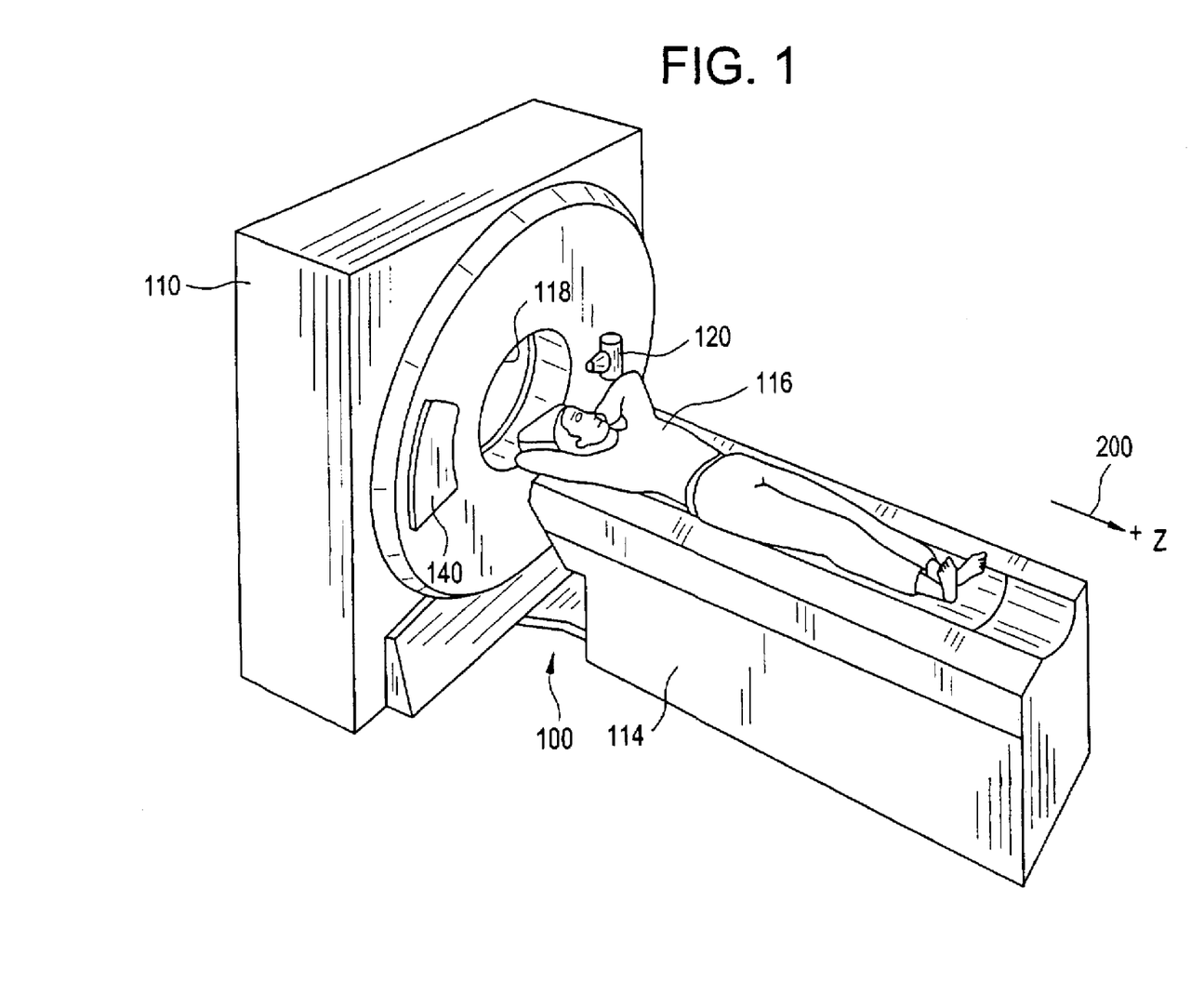
FIG. 1 depicts a generalized pictorial view of a CT imaging system for use in an embodiment of the present invention.
Figure 2:
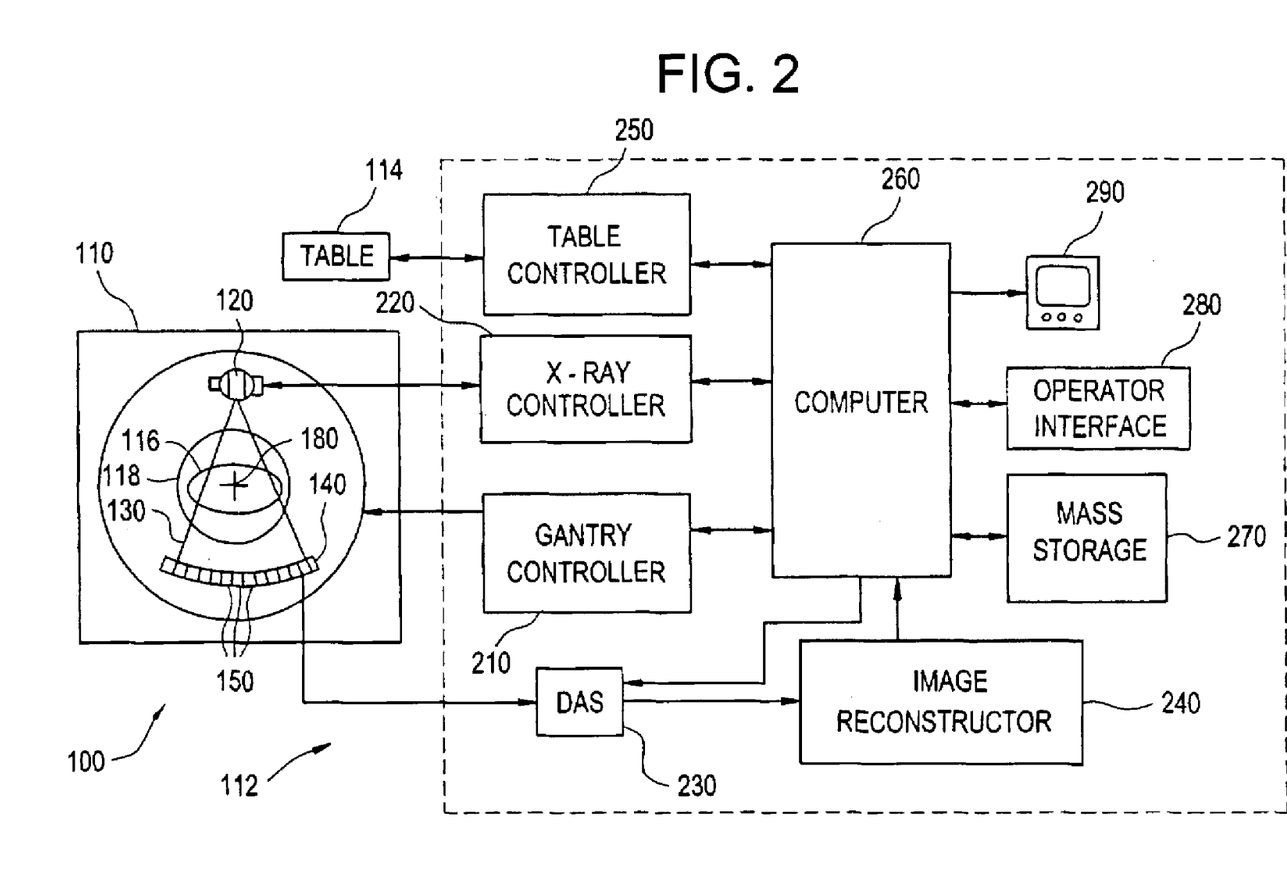
FIG. 2 depicts a generalized block schematic diagram of the imaging system of FIG. 1.

Referring to FIGS. 1 and 2, a computed tomography (CT) imaging system 100 is shown having a gantry 110, which is representative of a CT scanner, a control system 112, and a motorized table 114 for positioning an object 116, such as a patient, in gantry opening 118 in gantry 110. Gantry 110 includes an x-ray source that projects a fan beam of x-rays 130 toward a detector array 140 on the opposite side of gantry 110. Detector array 140 is formed by detector elements 150, which may include a single row or multiple rows of elements 150. Detector elements 150 are radiation detectors that each produce a signal having a magnitude that represents and is dependent on the intensity of the attenuated x-ray beam after it has passed through patient 116 being imaged. During a scan that acquires x-ray projection data, the gantry 110 along with the x-ray source 120 and detector array 140 rotate within the imaging plane and around the patient 116 about a center of rotation 180, while the patient 116 is moved through the gantry in a negative z-direction 200 perpendicular to the imaging plane.

Gantry 110 and x-ray source 120 are controlled by control system 112, which includes a gantry controller 210, an x-ray controller 220, a data acquisition system (DAS) 220, an image reconstructor 240, a table controller 250, a computer 260, a mass storage system 270, an operator interface 280, and a display device 290. Gantry controller 210 controls the rotational speed and position of gantry 110, x-ray controller 220 provides power and timing signals to x-ray source 120, data acquisition system 220 acquires analog data from detector elements 150 and converts the data to digital form for subsequent processing, image reconstructor 240 receives the digitized x-ray data from DAS 230 and performs an image reconstruction process that involves volume scoring the concentration of calcification within a region of interest associated with a calcium lesion, as discussed below, and table controller 250 that controls motorized table 114 to position patient 116 in gantry opening 118.

Computer 260 is in operable communication with gantry controller 210, x-ray controller 220, and table controller 250 whereby control signals are sent from the computer to controllers 210, 220, 250 and information is received from the controllers by computer 260. Computer 260 also provides commands and operational parameters to DAS 230 and receives reconstructed image data from image reconstructor 240. The reconstructed image data is stored by computer 260 in a mass storage device 270 for subsequent retrieval. An operator interfaces with computer 260 through operator interface 280, which may include, for example, a keyboard and a graphical pointing device, and receives output, such as, for example, a reconstructed image, control settings and other information, on a display device 290.

Operable communication between the various system elements of FIG. 1 is depicted by arrowhead lines, which illustrate a means for either signal communication or mechanical operation, depending on the system element involved. Operable communication amongst and between the various system elements may be obtained through a hardwired or a wireless arrangement. Computer 260 may be a standalone computer or a network computer and may include instructions in a variety of computer languages for use on a variety of computer platforms, such as, for example, DOS-based systems, Apple-based systems, Windows-based systems, HTML-based systems, or the like.

Computer 260 performs post image-reconstruction analysis by applying a volume scoring algorithm, discussed in detail below in reference to FIG. 3, that more accurately reflects the actual concentration of calcification. In an alternative embodiment, DAS 230 and image reconstructor 240 may be integrated with computer 260.

An embodiment of the present invention employs a volume-scoring algorithm that takes into account a non-uniform concentration of calcification within the lesion. Certain volume-scoring techniques, such as, for example, region-of-interest volume-scoring, are known in the art, however, concentration volume-scoring is performed in an embodiment of the present invention and involves the introduction of a regression line slope into the volume-scoring algorithm. A flowchart for implementing the concentration volume-scoring process in accordance with an embodiment of the invention is depicted in FIG. 3.

Figure 3:
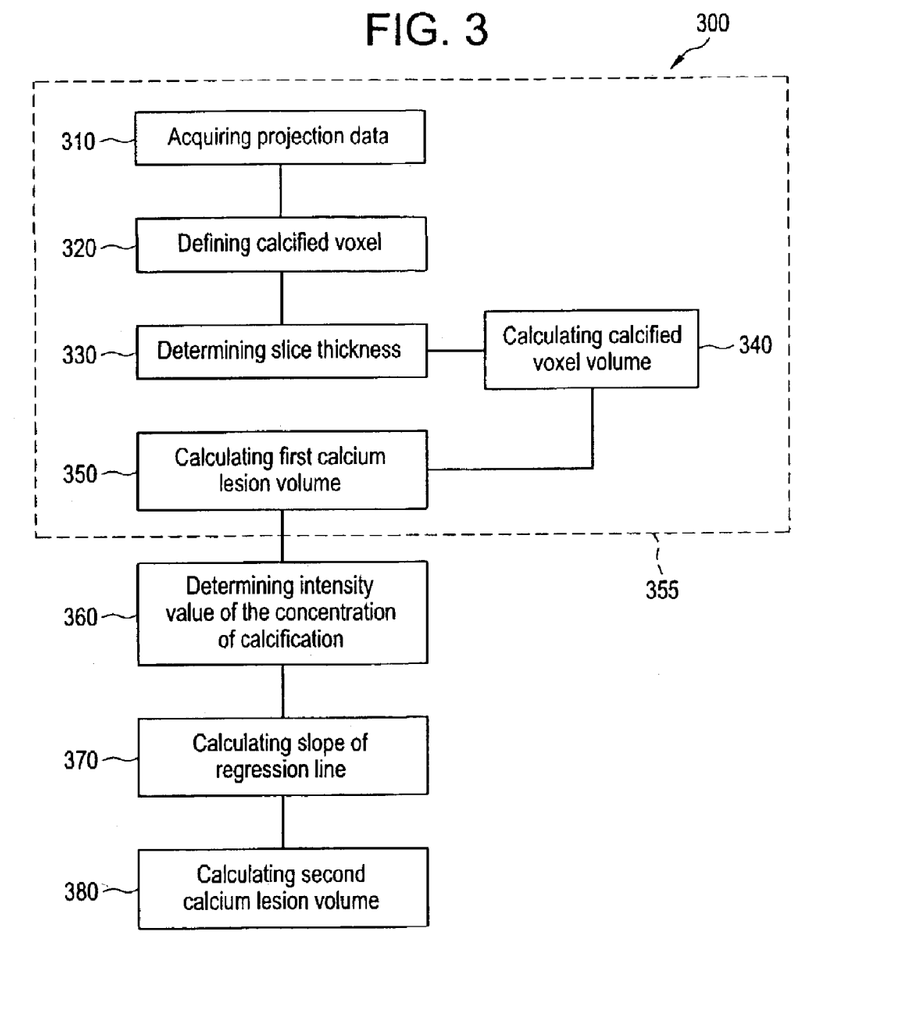
FIG. 3 depicts a process flowchart for implementing the volume-scoring method in an embodiment of the present invention.

Referring now to FIG. 3, process 300 begins with the acquisition 310 of projection data representative of the calcium concentration of a scan of an object, such as a calcium concentration within patient 116, using CT system 100, control system 112 and table 114, and specifically using DAS 230.

Using DAS 230 and image reconstructor 240, calcified voxels within a region of interest are defined 320 based on the acquired projection data by identifying those voxels within the region of interest that have attenuation values greater than a specified intensity and connectivity criteria. As the x-ray beam passes through patient 116, the signal strength attenuates as a function of the concentration of calcification. The attenuation of the X-ray beam is proportional to the concentration of the calcium within the calcified area. Signal attenuation levels of greater than about 130 Hounsfield Units signifies a region of calcification, thereby establishing a signal attenuation threshold criteria of about 130 HU. Other thresholds may be employed depending on the analysis being pursued. The intensity of the calcium lesion may go up as high as about 800 HU, or higher. The connectivity criteria is based upon the intensity value of adjacent pixels. For a specific pixel, if adjacent pixels exhibit intensity values above the threshold, the specified pixel is considered to depict a valid calcified point. For calcification studies, a connectivity value of 2, i.e. two adjacent pixels having Hounsfield numbers greater than the threshold, is typically employed. However, other pixel connectivity values may be employed depending on the analysis being pursued. Thus, an embodiment of the present invention considers calcified voxels within a region of interest to be those voxels having a signal attenuation of greater than about 130 HU and a pixel connectivity value of 2.

At step 330, the slice thickness of the acquired projection data is determined. The slice thickness is determined by the speed at which DAS 230 acquires the projection data and by the operating parameters of computer 260, gantry controller 210 and table controller 250. An operator at operator interface 280 may change the operating parameters depending on the analysis being pursued. Slice thickness typically, but not necessarily, vary between about 1.25 and about 5 millimeters (mm). A smaller slice thickness is preferred, but a smaller thickness requires more images and longer scan time. A slice thickness of about 2.5 mm or less is generally preferred. For overlapping slices, the slice thickness is adjusted by the slice spacing, or alternatively, is reduced by the percentage of overlap between two adjacent slices.

At step 340, image reconstructor 240 and computer 260 calculate the volume of each calcified voxel. The volume of a calcified voxel is determined by multiplying the pixel area of a calcified voxel by the slice thickness. The volume score is expressed in $cm^3$ (cubic centimeters, cc) for each slice.

At step 350, image reconstructor 240 and computer 260 calculate a first calcium lesion volume by adding together each volume of calcified voxels from step 340.

Steps 310–350 may be combined into one process step where computer 260 receives 355 a calculation for a first calcium lesion volume.

At step 360, image reconstructor 240 and computer 260 determine an intensity value of the concentration of calcification within the region of interest by analyzing the pixel intensities within the region of interest for a mean, average, or weighted average intensity value.

Figure 4:
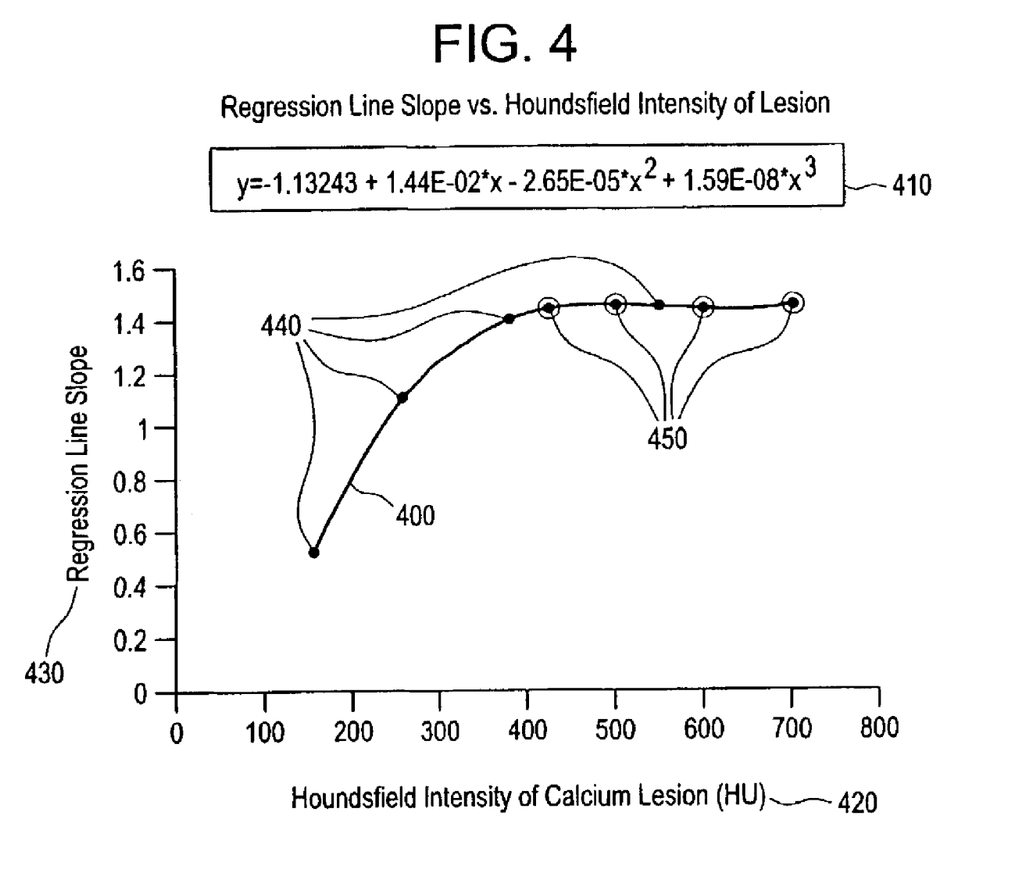
FIG. 4 depicts a graphical representation of a regression line slope as a function of calcium lesion intensity for use in an embodiment of the present invention.

At step 370, computer 260 calculates a regression curve based on the determined intensity value from step 360. FIG. 4 depicts a graphical representation (best-fit-curve) 400 of a function y(x) 410 in accordance with an embodiment of the invention, where x represents the intensity of calcium lesion in HU 420, and y represents the regression slope 430. FIG. 4 shows two types of data points: measured data points 440 and weighting data points 450. The measured data points 440 were obtained experimentally, as discussed below. The weighting data points 450 were added in order to weight a best-fit-curve of a regression line slope to more accurately fit the measured data points 440. Table-1 shows the data points 440, 450 and the associated regression line slope.

TABLE 1

| Data Point Type | Mean Intensity (HU) | Slope of Regression Line |
|---|---|---|
| 440 | 155 | 0.522 |
| 440 | 256 | 1.1091 |
| 440 | 379 | 1.406 |
| 450 | 425 | 1.45 |
| 450 | 500 | 1.45 |
| 440 | 550 | 1.4463 |
| 450 | 600 | 1.45 |
| 450 | 700 | 1.45 |

The function y(x) 410 represents the equation for the best-fit-curve 400, which is provided below as Equation-1.

$$y = -1.13243 + 1.44E\text{-}02*x - 2.65E\text{-}05*x^2 - 1.59E\text{-}08*x^3 \quad \text{Equa. 1.}$$

It will be appreciated that the introduction of weighting data points 450 impact the value of the coefficients for the "x" terms, and that Equation-1 may be written with fewer or more "x" terms depending on the curve-fit employed. Accordingly, Equation-2 depicts a more general form of Equation-1, $$y = a + b*x + c*x^2 + d*x^3 + \ldots \quad \text{Equa. 2.}$$

where coefficients a, b, and c are determined by the curve-fit algorithm employed and the resulting coefficients, which may include zero, and "..." signifies the option of including higher order "x" terms in the curve-fit equation. Equation-2 is typically non-linear, but depending on the curve-fit coefficients employed, Equation-2 could also be linear. Computer 260 applies Equation-1 to the mean intensity value from step 360 to yield a regression line slope.

At step 380, computer 260 calculates a second calcium lesion volume based on the first calcium lesion volume and the calculated slope of the regression line by dividing the first calcium lesion volume by the calculated value for y from Equation-1 in step 370. By introducing a regression line slope into the calcium lesion volume calculation, a reduction in error of calculated-to-actual calcium lesion volume can be achieved. Without the introduction of a regression line slope, the calculated-to-actual calcium lesion volume error may be +30% to −40%. With the introduction of a regression line slope, the error (score accuracy error) is substantially reduced to within about +/−10% (that is, equal to or greater than about −10% and equal to or less than about +10%), thereby providing a more accurate depiction of the concentration of calcification within patient 116.

Figure 5:
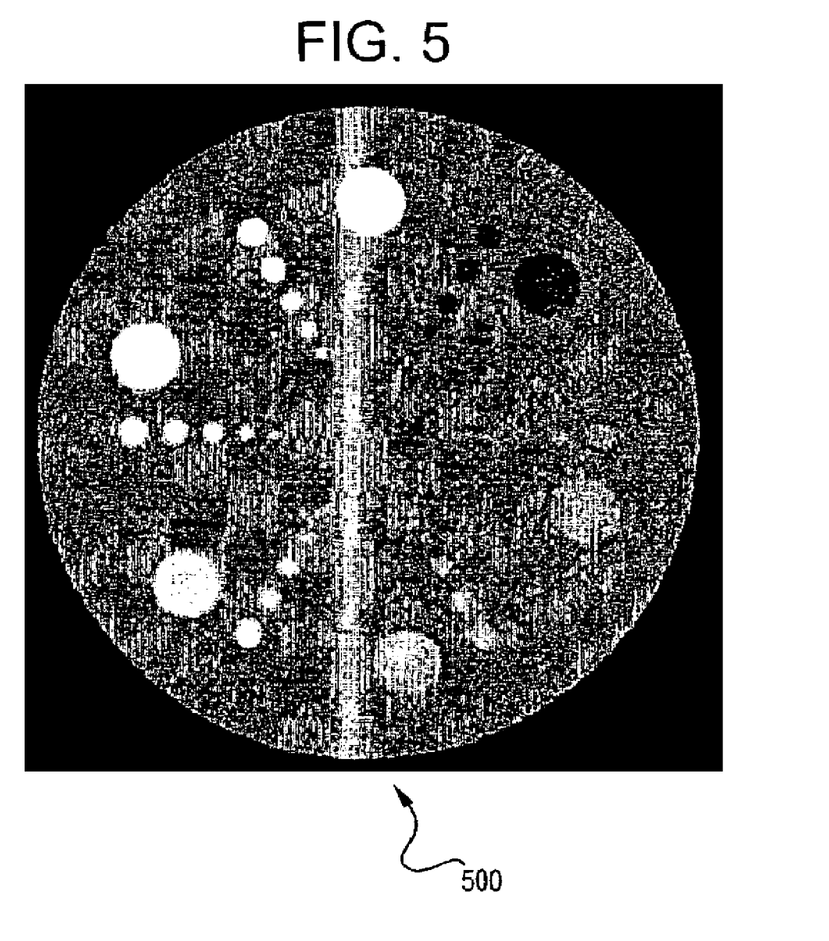
FIG. 5 depicts a graphical representation of a scanned phantom used for generating the graphical representation of FIG. 4.

Referring back to FIG. 4 and Table-1, measured data points 440 were determined experimentally using a new phantom consisting of six sets of plastic rods embedded in a 25 centimeter (cm) diameter plastic core. Each set of rods had 2, 3, 4, 5, 6 and 15 mm diameter rods. The plastic core had an attenuation of 60 HU and the rod sets had attenuations of 0, 110, 150, 250, 350 and 450 HU. The phantom was scanned in an axial mode at a tube voltage of 120 Kilivolts (KV). The tube currents ranged from 50–440 milliamps (ma), and slice thicknesses of 1.25, 2.5, 3.75 and 5 mm were used. For some trials, the phantom was placed inside an oval shaped attenuation ring to simulate the effect of attenuation by surrounding tissues and bones. The scan images were reconstructed using a Half Scan Algorithm and scored using a modified Agatston Janowitz method with a minimal attenuation threshold of 130 HU and a 2 pixel connectivity. The scores were divided into three categories: low (<50 HU), medium (51–200 HU), and high (>200 HU). Analysis of the scores resulted in the data shown in Table-1 and the regression line slope depicted in FIG. 3. FIG. 5 depicts a reconstructed scan image of the cross-section of the new phantom 500 used in the experiment discussed above.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for volume scoring a concentration of calcification within a region of interest, comprising:
   receiving a value for a first calcium lesion volume based on the concentration of calcification within the region of interest;
   determining an intensity value of the concentration of calcification within the region of interest;
   calculating the slope of a regression line based on the determined intensity value; and calculating a second calcium lesion volume based on the first calcium lesion volume and the calculated slope of the regression line.

2. The method for volume scoring a concentration of calcification set forth in claim 1, wherein said receiving a value for a first calcium lesion volume comprises:
   acquiring projection data representing the calcium concentration of a CT scan of an object;
   defining a calcified voxel within the region of interest based on the acquired projection data;
   determining a slice thickness of the acquired projection data;
   calculating a calcified voxel volume based on the pixel area of the calcified voxel and the slice thickness of the acquired projection data; and
   calculating a first calcium lesion volume based on the calculated calcified voxel volume.

3. The method for volume scoring set forth in claim 1, wherein said determining an intensity value further comprises:
   determining a mean intensity value.

4. The method for volume scoring set forth in claim 1, wherein said calculating a second calcium lesion volume further comprises:
   calculating a second calcium lesion volume having a score accuracy error equal to or greater than about −10% and equal to or less than about +10%.

5. The method for volume scoring set forth in claim 2, wherein said determining a slice thickness further comprises:
   determining a slice thickness equal to or greater than about 1.25 millimeters and equal to or less than about 5 millimeters.

6. The method for volume scoring set forth in claim 5, wherein said determining a slice thickness further comprises:
   determining a slice thickness equal to or greater than about 1.25 millimeters and equal to or less than about 2.5 millimeters.

7. The method for volume scoring set forth in claim 2, wherein said defining a calcified voxel within the region of interest further comprises:
   defining a calcified voxel within the region of interest based on a signal attenuation threshold and a pixel connectivity value.

8. The method for volume scoring set forth in claim 7, wherein said defining a calcified voxel within the region of interest further comprises:
   defining a calcified voxel within the region of interest based on a signal attenuation of greater than about 130 Hounsfield Units and a pixel connectivity value of 2.

9. The method for volume scoring set forth in claim 2, wherein said determining a slice thickness further comprises;
   adjusting the slice thickness by the slice spacing for overlapping slices.

10. A method for volume scoring a concentration of calcification within a region of interest, comprising:
    receiving a value for a first calcium lesion volume based on the concentration of calcification within the region of interest;
    determining an intensity value of the concentration of calcification within the region of interest;
    calculating the slope of a regression line based on the determined intensity value and according to a non-linear function (y); and
    calculating a second calcium lesion volume based on the first calcium lesion volume and the calculated slope of the regression line.

11. The method for volume scoring set forth in claim 10, wherein said calculating a second calcium lesion volume further comprises:
    calculating a second calcium lesion volume according to the following equation (second calcium lesion volume)=(first calcium lesion volume)/($y$).

12. The method for volume scoring set forth in claim 10, wherein said calculating the slope of a regression line further comprises:
    calculating the slope of a regression line based on measured data points and weighting data points.

13. A method for volume scoring a concentration of calcification within a region of interest, comprising:
    receiving a value for a first calcium lesion volume based on the concentration of calcification within the region of interest;
    determining an intensity value of the concentration of calcification within the region of interest;
    calculating the slope of a regression line based on the determined intensity value and according to the following equation $y = -1.13243 + 1.44E{-}02 * x - 2.65E{-}05 * x^2 + 1.59E{-}08 * x^3$ wherein x represents the mean intensity value of the concentration of calcification within the region of interest in Hounsfield Units and y represents the slope of the regression line; and
    calculating a second calcium lesion volume based on the first calcium lesion volume and the calculated slope of the regression line.

14. The method for volume scoring set forth in claim 13, wherein said calculating a second calcium lesion volume further comprises:
    calculating a second calcium lesion volume according to the following equation second calcium lesion volume=(first calcium lesion volume)/$y$.

15. A system for volume scoring a concentration of calcification within a region of interest, said system comprising a computer programmed to:
    receive a value for a first calcium lesion volume based on the concentration of calcification within the region of interest;
    determine an intensity value of the concentration of calcification within the region of interest;
    calculate the slope of a regression line based on the measured intensity value; and
    calculate a second calcium lesion volume based on the first calcium lesion volume and the calculated slope of the regression line.

16. The system for volume scoring of claim 15, wherein said system comprising a computer programmed to receive a value for a first calcium lesion volume comprises the computer programmed to:
    acquire projection data representing the calcium concentration of a CT scan of an object;
    define a calcified voxel within the region of interest based on the acquired projection data;
    determine a slice thickness of the acquired projection data;

calculate a calcified voxel volume based on the pixel area of the calcified voxel and the slice thickness of the acquired projection data; and calculate a first calcium lesion volume based on the calculated calcified voxel volume.

17. The system for volume scoring of claim 15, wherein said system comprising a computer programmed to determine an intensity value further comprises the computer programmed to:

determine a mean intensity value.

18. The system for volume scoring of claim 15, wherein said system comprising a computer programmed to calculate the slope of a regression line further comprises the computer programmed to:

calculate the slope of a regression line according to the following equation:

$$y=-1.13243+1.44E-02*x-2.65E-05*x^2+1.59E-08*x^3;$$

wherein x represents the mean intensity value of the concentration of calcification within the region of interest in Hounsfield Units and y represents the slope of the regression line.

19. The system for volume scoring of claim 18, wherein said system comprising a computer programmed to calculate a second calcium lesion volume further comprises the computer programmed to:

calculate a second calcium lesion volume according to the following equation:

second calcium lesion volume=(first calcium lesion volume)/y.

20. The system for volume scoring of claim 15, wherein said system comprising a computer programmed to calculate a second calcium lesion volume further comprises the computer programmed to:

calculate a second calcium lesion volume having a score accuracy error equal to or greater than about −10% and equal to or less than about +10%.

21. The system for volume scoring of claim 16, wherein said system comprising a computer programmed to determine a slice thickness further comprises the computer programmed to:

determine a slice thickness equal to or greater than about 1.25 millimeters and equal to or less than about 5 millimeters.

22. The system for volume scoring of claim 21, wherein said system comprising a computer programmed to determine a slice thickness further comprises the computer programmed to:

determine a slice thickness equal to or greater than about 1.25 millimeters and equal to or less than about 2.5 millimeters.

23. The system for volume scoring of claim 16, wherein said system comprising a computer programmed to define a calcified voxel within a region of interest further comprises the computer programmed to:

define a calcified voxel within a region of interest based on a signal attenuation threshold and a pixel connectivity value.

24. The system for volume scoring of claim 23, wherein said system comprising a computer programmed to define a calcified voxel within a region of interest further comprises the computer programmed to:

define a calcified voxel within a region of interest based on a signal attenuation of greater than about 130 Hounsfield Units and a pixel connectivity value of 2.

25. The system for volume scoring of claim 16, wherein said system comprising a computer programmed to determine a slice thickness further comprises the computer programmed to:

adjust the slice thickness by the slice spacing for overlapping slices.

26. A system for volume scoring a concentration of calcification within a region of interest, said system comprising a computer programmed to:

receive a value for a first calcium lesion volume based on the concentration of calcification within the region of interest;

determine an intensity value of the concentration of calcification within the region of interest;

calculate the slope of a regression line based on the measured intensity value and according to a non-linear function (y); and calculate a second calcium lesion volume based on the first calcium lesion volume and the calculated slope of the regression line.

27. The system for volume scoring set forth in claim 26, wherein said system comprising a computer programmed to calculate a second calcium lesion volume further comprises the computer programmed to:

calculate a second calcium lesion volume according to the following equation (second calcium lesion volume)=(first calcium lesion volume)/(y).

28. The system for volume scoring of claim 26, wherein said system comprising a computer programmed to calculate the slope of a regression line further comprises the computer programmed to:

calculate the slope of a regression line based on measured data points and weighting data points.

* * * * *

UNITED STATES PATENT AND TRADEMARK OFFICE
CERTIFICATE OF CORRECTION

| | |
|---|---|
| PATENT NO. | : 7,239,730 B2 |
| APPLICATION NO. | : 10/248562 |
| DATED | : July 3, 2007 |
| INVENTOR(S) | : Londt et al. |

It is certified that error appears in the above-identified patent and that said Letters Patent is hereby corrected as shown below:

Column 1:
Line 54, after "cm" delete " $^2$ " and insert therefor -- $^3$ --

Signed and Sealed this

Thirtieth Day of October, 2007

JON W. DUDAS
*Director of the United States Patent and Trademark Office*